United States Patent
Barre et al.

(10) Patent No.: US 12,076,433 B2
(45) Date of Patent: Sep. 3, 2024

(54) PHARMACEUTICAL BENEFITS MANAGEMENT

(71) Applicant: MEDIMPACT HEALTHCARE SYSTEMS, INC., San Diego, CA (US)

(72) Inventors: William J. Barre, San Diego, CA (US); Dale R. Brown, Poway, CA (US); Frederick Howe, Rancho Santa Fe, CA (US)

(73) Assignee: MEDIMPACT HEALTHCARE SYSTEMS, INC., San Diego, CA (US)

( * ) Notice: Subject to any disclaimer, the term of this patent is extended or adjusted under 35 U.S.C. 154(b) by 0 days.

(21) Appl. No.: 17/698,945

(22) Filed: Mar. 18, 2022

(65) Prior Publication Data

US 2022/0344021 A1 Oct. 27, 2022

Related U.S. Application Data

(60) Continuation of application No. 12/841,103, filed on Jul. 21, 2010, now Pat. No. 11,865,199, which is a
(Continued)

(51) Int. Cl.
*A61K 8/66* (2006.01)
*A61K 8/73* (2006.01)
(Continued)

(52) U.S. Cl.
CPC ............ *A61K 8/66* (2013.01); *A61K 8/732* (2013.01); *A61Q 19/08* (2013.01); *G06Q 30/06* (2013.01); *G06Q 40/08* (2013.01); *G16H 20/10* (2018.01)

(58) Field of Classification Search
CPC .......... A61K 8/66; A61K 8/732; A61Q 19/08; G06Q 30/06; G06Q 40/08; G16H 20/10
See application file for complete search history.

(56) References Cited

U.S. PATENT DOCUMENTS 5,301,105 A 4/1994 Cummings, Jr.
5,704,044 A 12/1997 Tarter et al.
(Continued)

FOREIGN PATENT DOCUMENTS

JP 2003263499 A 9/2003
KR 20010075839 A 8/2001
(Continued)

OTHER PUBLICATIONS

(Oct. 2007) AMCP Guide to Pharmaceutical Payment Methods; Comperhensive Edition; AMCP Task Force on Drug Payment Methodologies; 65 pages.
(Continued)

*Primary Examiner* — Eliza A Lam
(74) *Attorney, Agent, or Firm* — Mintz Levin Cohn Ferris Glovsky and Popeo, P.C.

(57) ABSTRACT

Systems, devices, non-transitory computer storage mediums, and methods are described herein for pharmaceutical benefits management including routing pharmaceutical claims over a computer network. The system includes a computer network and a client device communicatively coupled to the computer network. The client device is configured to receive order information representative of a prescription drug prescribed for a consumer. The system includes a communications switch configured to derive a processor control number associated with the order information and route the order information based on the processor control number. The system includes a pharmaceutical benefits manager configured to authorize the prescription drug with the reimbursement based on the processor control number and configured to transmit the authorization with the reimbursement to the client device.

12 Claims, 2 Drawing Sheets

Related U.S. Application Data division of application No. 11/266,885, filed on Nov. 4, 2005, now abandoned.

(51) Int. Cl.
*A61Q 19/08* (2006.01)
*G06Q 30/06* (2023.01)
*G06Q 40/08* (2012.01)
*G16H 20/10* (2018.01)

(56) References Cited

U.S. PATENT DOCUMENTS

| | | | |
|---|---|---|---|
| 5,737,539 | A | 4/1998 | Edelson et al. |
| 5,845,255 | A | 12/1998 | Mayaud |
| 6,108,635 | A | 8/2000 | Herren et al. |
| 6,195,612 | B1 | 2/2001 | Pack-harris |
| 6,283,761 | B1 | 9/2001 | Joao |
| 6,341,265 | B1 | 1/2002 | Provost et al. |
| 7,165,077 | B2 | 1/2007 | Kalies |
| 7,412,396 | B1 | 8/2008 | Haq |
| 7,490,047 | B2 | 2/2009 | Brown et al. |
| 7,505,917 | B2 | 3/2009 | Howe et al. |
| 7,685,026 | B1 | 3/2010 | Mcgrady et al. |
| 7,769,601 | B1 | 8/2010 | Bleser et al. |
| 7,840,424 | B2 | 11/2010 | Wiley et al. |
| 7,949,580 | B1 | 5/2011 | Boyer et al. |
| 8,060,379 | B1 | 11/2011 | Pinsonneault et al. |
| 8,069,059 | B2 | 11/2011 | Howe et al. |
| 8,099,295 | B2 | 1/2012 | Virdee et al. |
| 8,265,950 | B2 | 9/2012 | Howe et al. |
| 8,346,571 | B2 | 1/2013 | Kalies, Jr. |
| 8,447,628 | B2 | 5/2013 | Kalies, Jr. |
| 8,788,282 | B2 | 7/2014 | Watanabe |
| 2001/0037216 | A1 | 11/2001 | Oscar et al. |
| 2002/0002495 | A1 | 1/2002 | Ullman |
| 2002/0049617 | A1 | 4/2002 | Lencki et al. |
| 2002/0082863 | A1 | 6/2002 | Kleinke |
| 2002/0095316 | A1 | 7/2002 | Toan et al. |
| 2002/0111832 | A1 | 8/2002 | Judge |
| 2002/0120473 | A1 | 8/2002 | Wiggins |
| 2002/0147617 | A1 | 10/2002 | Schoenbaum et al. |
| 2002/0169727 | A1 | 11/2002 | Melnick et al. |
| 2002/0183965 | A1 | 12/2002 | Gogolak |
| 2003/0154106 | A1 | 8/2003 | Marks |
| 2003/0195771 | A1 | 10/2003 | Fitzgerald et al. |
| 2004/0039604 | A1 | 2/2004 | Tallal |
| 2004/0054685 | A1 | 3/2004 | Rahn et al. |
| 2004/0073457 | A1 | 4/2004 | Kalies |
| 2004/0122713 | A1 | 6/2004 | Hill et al. |
| 2004/0133452 | A1 | 7/2004 | Denny et al. |
| 2004/0143171 | A1 | 7/2004 | Kalies |
| 2004/0143594 | A1 | 7/2004 | Kalies |
| 2004/0148194 | A1 | 7/2004 | Wellons et al. |
| 2004/0148195 | A1 | 7/2004 | Kalies |
| 2004/0148196 | A1 | 7/2004 | Kalies |
| 2004/0148198 | A1 | 7/2004 | Kalies |
| 2004/0148498 | A1 | 7/2004 | Circenis et al. |
| 2004/0153336 | A1* | 8/2004 | Virdee .................. G06Q 10/10 705/2 |
| 2004/0165725 | A1 | 8/2004 | Kumar et al. |
| 2004/0230502 | A1 | 11/2004 | Fiacco et al. |
| 2005/0060188 | A1 | 3/2005 | Valley |
| 2005/0065821 | A1 | 3/2005 | Kalies, Jr. |
| 2005/0071193 | A1 | 3/2005 | Kalies |
| 2005/0071200 | A1 | 3/2005 | Franklin et al. |
| 2005/0240442 | A1 | 10/2005 | Lapsker |
| 2005/0251429 | A1 | 11/2005 | Ammer et al. |
| 2005/0261939 | A1 | 11/2005 | Augspurger et al. |
| 2005/0283259 | A1 | 12/2005 | Wolpow |
| 2006/0020514 | A1 | 1/2006 | Yered |
| 2006/0116905 | A1 | 6/2006 | Yered |
| 2006/0129357 | A1 | 6/2006 | Francis et al. |
| 2006/0178915 | A1 | 8/2006 | Chao et al. |
| 2006/0182705 | A1 | 8/2006 | Cruse |
| 2006/0184391 | A1 | 8/2006 | Barre et al. |
| 2006/0271402 | A1 | 11/2006 | Rowe et al. |
| 2007/0011025 | A1 | 1/2007 | Cracchiolo et al. |
| 2007/0025031 | A1 | 2/2007 | Kwon |
| 2007/0050210 | A1 | 3/2007 | Wiley |
| 2007/0106623 | A1 | 5/2007 | Melnick et al. |
| 2007/0233516 | A1 | 10/2007 | Howe et al. |
| 2007/0233526 | A1 | 10/2007 | Hoffman et al. |
| 2007/0250341 | A1 | 10/2007 | Howe et al. |
| 2008/0183492 | A1 | 7/2008 | Warren et al. |
| 2008/0228519 | A1 | 9/2008 | Leon |
| 2008/0312956 | A1 | 12/2008 | Momita et al. |
| 2009/0076868 | A1 | 3/2009 | Malone et al. |
| 2009/0144082 | A1 | 6/2009 | Selbst et al. |
| 2009/0177488 | A1 | 7/2009 | Unland et al. |
| 2009/0177490 | A1 | 7/2009 | Howe et al. |
| 2009/0281823 | A1 | 11/2009 | Hardaway |
| 2009/0281824 | A1 | 11/2009 | Hardaway |
| 2009/0319311 | A1 | 12/2009 | Mi et al. |
| 2009/0326975 | A1 | 12/2009 | Hardaway et al. |
| 2010/0057489 | A1 | 3/2010 | Howe et al. |
| 2010/0161351 | A1 | 6/2010 | Howe et al. |
| 2010/0217622 | A1 | 8/2010 | Brown et al. |
| 2010/0287002 | A1 | 11/2010 | Barre et al. |
| 2010/0312578 | A1 | 12/2010 | Hardaway |
| 2011/0029321 | A1 | 2/2011 | Rourke et al. |
| 2011/0054935 | A1 | 3/2011 | Hardaway |
| 2012/0253829 | A1 | 10/2012 | John et al. |
| 2014/0278495 | A1 | 9/2014 | Rourke et al. |
| 2016/0034668 | A1 | 2/2016 | Rourke et al. |
| 2017/0161458 | A1 | 6/2017 | Rourke et al. |

FOREIGN PATENT DOCUMENTS

| | | |
|---|---|---|
| WO | 9524010 A1 | 9/1995 |
| WO | 9744752 A1 | 11/1997 |
| WO | 2014151911 A1 | 9/2014 |

OTHER PUBLICATIONS (Oct. 27, 2006) Bank of America and Caremark introduce pharma rewards credit card, http://www.banking-business-review.com/news/bank_of_america_and_caremark_introduce_pharma_r, 1 page.

(Jul. 2006) Centers for Medicare & Medicaid Services (CMS), 2006 Prescription Drug Event Data Training Participant Guide, pp. 1-222.

(May 11, 2006) CitiBusiness Credit Cards Free Prescription Discount Program, 07:14 AM Pacific http://www.paymentsnews.com/2006/05/citibusiness_cr.html, 3 pages.

(May 11, 2006) CitiBusiness(R) Credit Cards Announces New Card member Benefit Free Prescription Discount Program, http:/Mw-N.prnewswire.com/cgi-bin/stories.pl?ACCT=104&STORY=/ww, 2 pages.

(Nov. 24, 2006) Comments of Generic Pharmaceutical Association for the Public Meeting on Proposed Changes to the National Drug Code System, Docket No. 2005N-0403; RIN 0910-AA49, 7 pages.

Cost Sharing Strategies for OHP Medical Services, revised Jul. 5, 2001, pp. 1-5.

Credit Cards Offer Discounts on Prescription Drugs, http://wbztv.com/consumer/credit.Card.Discounts.2.682345.html, Mar. 26, 2008, 2 pages.

(Jul. 14, 2006) CVS to Buy MinuteClinic Walk-In Medical Service, Los Angeles Times, 1 page.

(2008) Florida House of Representatives, Enrolled CS/HB 535, Legislature, 5 pages.

International Search Report and Written Opinion received for PCT Patent International Application No. PCT/US2006/042976, mailed on Jul. 8, 2007, 9 pages.

(Mar. 25, 2008) MedImpact Medicare Part D 2008 Pre-Processing Drug List (PPDL) White Paper, pp. 1-5.

(Mar. 25, 2008) MedImpact Medicare Part D 2009 Pre-Processing Drug List (PPDL) White Paper, pp. 1-5.

(Oct. 13, 2005) MedImpact Medicare Part D Drug List White Paper, pp. 1-4.

(Jul. 20, 2006) MedImpact Medicare Part D Pre-Processing Drug List (PPDL) White Paper, Updated, pp. 1-5.

International Preliminary Report on Patentability received for Application No. PCT/US2014/026660, mailed on Sep. 15, 2015, 6 pages.

(56) References Cited

OTHER PUBLICATIONS

International Search Report and Written Opinion for Application No. PCT/US2014/026660, mailed on Aug. 4, 2014, 8 pages.

(Jun. 6, 2009) Prescription Card, Available on: https://www.unionplus.org/benefits/health/prescriptions, 2 pages.

(Nov. 9, 2005) Systems Xcellence Announces Three-Year $4.0 Million Software License, Support and Operations Contract, 2 pages.

(Jun. 10, 2009) Walgreens Store Green Dot Prepaid MasterCard and Visa cards, Available on: http://www.walgreens.com/store/promotion/greendot/default.jsp, 2 pages.

Department of Health and Human S, (Apr. 27, 2006) "Requirements for Submitting Prescription Drug Event (PDE) Data", Centers for Medicare and Medicaid Services, pp. 1-94.

Federal Register, (May 16, 2008) "Medicare Program; Revisions to the Medicare Advantage and Prescription Drug Benefit Programs", Department of Health and Human Services (Hhs), 73(96):28556-28604.

Huskamp et al. (Mar.-Apr. 2000) "The Medicare Prescription Drug Benefit: How Will the Game be Played?", Health Affairs, 19(2):8-23.

Laing et al. (Feb. 2007) "Tuberculosis Drug Issues: Prices, Fixed Dose Combination Products and Second Line Drugs", Journal Tuberculosis Disease, 4(12):S194-S207 (26 pages).

Lipton et al. (Mar.-Apr. 2000) "Managing the Pharmacy Benefit in Medicare HMOs: What Do We Really Know?", Health Affairs, 19(2):42-58 (17 pages).

Infocrossing Healthcare Services, (2007) "Prescription Drug Event (PDE) Submission Process Summary", Infocrossing, pp. 1-2.

\* cited by examiner

PHARMACEUTICAL BENEFITS MANAGEMENT

CROSS REFERENCE TO RELATED APPLICATION

This application claims the benefit of and priority to and is a continuation of U.S. patent application Ser. No. 12/841,103, filed on Jul. 21, 2010, entitled "METHOD FOR PROVIDING CONSUMER CHOICE AND EQUALIZING PHARMACY PROVIDER AVAILABILITY IN PRESCRIPTION MEDICATION DISPENSING PLANS," which is a division of U.S. patent application Ser. No. 11/266,885, filed on Nov. 4, 2005, entitled "METHOD FOR PROVIDING CONSUMER CHOICE AND EQUALIZING PHARMACY PROVIDER AVAILABILITY IN PRESCRIPTION MEDICATION DISPENSING PLANS," the entirety of each of which is incorporated by reference herein.

FIELD

The disclosed subject matter is directed to systems and methods for routing claims over a network. More particularly, the technology relates to computer architecture and operating methods for pharmaceutical benefits management, including routing pharmaceutical claims over a computer network.

BACKGROUND

Computing systems can include a processor, a memory, a storage device, and input/output devices. The processor, the memory, the storage device, and the input/output devices can be interconnected via a system bus. The processor is capable of processing instructions for execution within the computing system. Such executed instructions can implement one or more components of, for example, a cloud platform. The computing system may include input/output devices that can provide input/output operations for a network device. For example, the input/output device can include Ethernet ports or other networking ports to communicate with one or more wired and/or wireless networks (e.g., a local area network (LAN), a wide area network (WAN), the Internet) or hardware or software implemented communications switches placed within the networked environment.

In conventional database systems, users access their data resources in one logical database. A user of such a conventional system typically retrieves data from and stores data on a local computing system. The local computing system might remotely access one of a plurality of server systems that might in turn access the database system over an electronic communications network. Data retrieval from the database system might include the issuance of a query from the user's local computing system to the database system. The database system might process the request for information received in the query and send to the user system information relevant to the request. The rapid and efficient retrieval of accurate information is critical to fulfilling prescription medication in a computer network environment in which a plurality of computing systems access and retrieve data from a plurality of databases coupled in a communications network.

Many employees and members ("patients") of health maintenance organizations, employer groups and government entities have their acquisitions of personal prescription medications subsidized by pharmacies through prescription benefit plans ("plans") offered by those health maintenance organizations, employer groups and government entities. Under such plans, a patient receives a prescription for a medication from his or her physician and submits it to a pharmacy to be filled. The pharmacy checks to see that the patient is a member of a plan with which the pharmacy has an agreement and that the medication and dosage prescribed are within the approved scope of the plan agreement. Upon verification of these requirements, the pharmacy dispenses the medication to the patient. The patient provides the pharmacy a "copay" amount, less than the normal cost of the medication. The pharmacy receives the balance of the payment for the medication and its dispensing services from the prescription benefit plan, which is managed by a "prescription benefit manager" ("PBM") with whom the health maintenance organization, employer group or government entity ("acquiring entity") has agreed to manage the plan. acquiring entity Medication usage is commonly differentiated between acute care usage, which is short term (30 days or less) administration to treat immediate illnesses or conditions, and maintenance usage, which is long term (more than 30 days) treatment of chronic illnesses or conditions such as hypertension, high cholesterol levels, arthritis, neurology conditions and the like. Maintenance medication dispensing and usage represents a major health care cost (on the order of 75% of prescription costs for many plans, especially due to the aging of the American population) and therefore control of maintenance prescription costs is a principal function of the prescription benefit plans.

Dispensing pharmacies are normally of two types: retail pharmacies (which are local neighborhood businesses where the patient appears in person, can meet with a pharmacist, requests his/her medication and can usually leave a few minutes later with the dispensed medication in hand) and mail order pharmacies (which are large facilities, usually not open to individual patient's personal visits, but from which a patient's medication order received by mail or through the Internet is subsequently filled and dispensed to the patient via mail or courier service). It is normally recognized by the industry that acute care prescriptions are dispensed primarily by retail pharmacies, since the patient frequently needs the medication immediately and cannot accept the multi-day delay inherent in submitting and dispensing prescription medications from the mail order pharmacies.

On the other hand, PBMs and benefit consultants commonly strongly urge or even mandate that patients in the plans that they administer obtain their maintenance medications from mail order pharmacies. It is a widely held belief that mail order pharmacies may have lower operating costs and may offer greater discounts available on medication coverage. To the extent that such is the case, use of mail order pharmacies may be a desirable cost control strategy if other contractual terms remain equalized. However, several factors can complicate the analysis of use of mail order pharmacies versus use of pharmacies especially for dispensing of maintenance medications.

For instance, some PBMs own mail order pharmacies, and therefore it is to their financial benefit to steer the patients in their plans to their captive pharmacies whether or not that is in the best interest of the patients. Further, to the extent that business is diverted unreasonably from pharmacies to mail order pharmacies, the former are deprived of income. Since the pharmacies are commonly localized businesses (in contrast to mail order pharmacies), their ability to survive to provide the local retail service is impaired. This is true even when a local pharmacy is part of a larger chain pharmacy organization, since decline in income of a local site could lead the chain to close that local site, notwithstanding that other locations of the chain's pharmacies remain in business.

Further, there are many variables in the pricing of medications and the costs involved in inventories, dispensing equipment, transportation of medications to the pharmacy and later to the patient and staffing that have been shown to affect whether mail order does or does not have a financial advantage over retail in the dispensing of medications. All that can be said is that, properly managed, both types can be financially and commercially viable. Significantly, there is a question of availability of choice for the consumer, since in many cases a patient would like to have the option of dealing either with his/her local pharmacy or a mail order pharmacy.

Numerous studies have established that for many prescription patients, direct contact with a pharmacist is very important. Professional pharmacists are held in very high regard by patients and their advice is eagerly sought. Most patients are not knowledgeable about medications and a prescribing physician's schedule may not provide sufficient time for a patient to be able to get what he or she believes to be sufficient information from the prescribing physician about all aspects of concern about a prescribed medication.

Patients want to be able to speak directly to their pharmacists for more information about their medications and receive detailed answers to their questions and concerns, especially when a maintenance medication which will be taken by the patient over a prolonged period is involved. It is well known that the prospects for a patient's successful implementation of a medication regimen are greatly enhanced when the patient understands and is comfortable with the medication prescribed. Such direct and personal contact with a pharmacist is frequently difficult for a patient to obtain from a mail order pharmacy, and even when available will almost certainly not involve a pharmacist who is "local" to the patient and his/her community.

Conventionally brand name prescriptions are priced by starting with a nationally published "average wholesale price" (AWP) and discounting this figure. A dispensing fee is then added to this number. A mail order or retail 90 day prescription is priced the same way with the exception that the mail order discounts are greater and there may or may not be a dispensing fee. On the other hand, in the prior art systems generic drug claims usually employ an additional variant for pricing. This is a concept known as "maximum allowable cost" (MAC) pricing. MAC is the concept of paying a set price for a product on a per unit basis.

Since multiple manufacturers may produce the same generic drug and dosage, the MAC price is applied regardless of the manufacturer or that particular manufacturer's AWP. In the prior art plans, it is common that 30-day prescriptions are paid at the lower of a) AWP minus a discount plus a dispensing fee or b) MAC plus a dispensing fee, while 90-day prescriptions are paid solely at AWP minus a discount. In the common situation where mail order pharmacies do not fill 30-day prescriptions and many 90-day prescription patients are routed by PBMs solely to mail order pharmacies, the system becomes biased, in that the patient and acquiring entity may actually pay more for one 90-day prescription compared to the dispensing of three 30-day prescription for a particular medication dispensed.

This leads to patient and acquiring entity dissatisfaction. The acquiring entity has an expectation of budgeting for a set discount for 90 day prescriptions since is the traditional 90 day method for reimbursement. When a lower of MAC or AWP model is used, an acquiring entity cannot guarantee an overall generic performance. The pharmacy has an expectation to be reimbursed a set amount for dispensing the 90-day prescription. When a lower of MAC or AWP model is used, the pharmacy cannot be sure of its reimbursement.

Prescription care plans function by assigning a "processor control number" (PCN) to each patient prescription claim. Since at present pharmacies typically dispense prescriptions in short-term (30-day or less) quantities and mail-order pharmacies dispense prescriptions in long-term (usually in either 60-day or 90-day) quantities, this means that a PBM is typically required to set up multiple PCNs for acute versus maintenance drug benefit designs, although each retail or mail order pharmacy is accustomed to identifying a single PCN to a patient prescription claim for a specific acquiring entity's plan.

As noted, patients and acquiring entities want to be able to choose where they get prescriptions filled. However, when a pharmacy undertakes to dispense both short-term and long-term quantities, the pharmacist or pharmacy staff must now in effect choose between two PCNs for the same acquiring entity. Since the patient only presents one identification card, this process can cause confusion at the pharmacy. This is counter productive to traditional workflow. It can cause confusion and delays at the point of sale transaction that impact both the patient and the pharmacy. It may also reduce the number of 90-day supply prescriptions that are filled at the retail level which impacts the cost structure for the acquiring entity.

It is not the intention of the disclosed subject matter to determine any conclusion as to the relative merits of mail order pharmacies versus pharmacies. Rather it is the intention of the disclosed subject matter to meet the long-felt and widely expressed desire by patients, acquiring entities and pharmacists to make both equally financially available under a prescription benefit plan such that patients can have a legitimate choice as to where and how they obtain their prescription medications, the acquiring entities will have a legitimate choice about how their contract plans will be structured, and pharmacists in both types of pharmacies can practice their profession successfully.

Accordingly, it is desirable to provide techniques enabling a claim routing system with a prescription benefits manager. It is also desirable to transmit data related to the prescription benefits manager so that a user has access to data that has been synchronized from another database system.

SUMMARY

For simplicity in the discussion below the disclosed subject matter will be described by division of prescription quantity fulfillments into two categories: a) "short term", "acute care" or "30-day" quantities, all of these terms being considered synonymous, and b) "long-term", "maintenance" or "90-day" quantities, all of these terms also being considered synonymous. Further, the terms "quantity", "quantity of dosage units" and "days supply" are also considered to be synonymous as applied to the number of medication pills, tablets, capsules, etc., or amount of medication liquid dispensed to the patient upon fulfillment of the prescription request. It will be understood, however, that these terms are so used for brevity and convenience, and that regardless of the choice of terminology the method of the disclosed subject matter is equally applicable to management of all prescription fulfillment and dispensing of medications in any dosages or quantities. Similarly, the particular total days supply of a dispensing prescription, whether the exemplary and commonly used 30- and 90-day quantities, or 14-, 60-, 100-day or any other quantities, is to be understood to be within the scope of the disclosed subject matter.

The disclosed subject matter provides an electronic system for routing claims. The system includes a computer network and a client device communicatively coupled to the computer network, the client device configured to receive order information representative of a prescription drug prescribed for a patient. The order information includes a given plan entity and a quantity. A communications switch is communicatively coupled to the client device via the computer network, the communications switch configured to derive a processor control number associated with the order information and route the order information based on the processor control number, the processor control number independent of the quantity of the prescription drug and configured to uniquely identify the prescription drug. A controller with a pharmaceutical benefits manager is communicatively coupled to the client device and the communications switch via the computer network. the pharmaceutical benefits manager is configured to approve the prescription drug and configured to determine a reimbursement. The controller is configured to receive, from the communications switch, the order information based on the processor control number and a business identification number, the business identification number configured to identify the pharmaceutical benefits manager among a plurality of pharmaceutical benefits managers. The controller is configured to determine, based on the pharmaceutical benefits manager, the reimbursement based on the order information. The controller is configured to determine, based on the pharmaceutical benefits manager, an authorization for the prescription drug with the reimbursement based on the processor control number. The controller is configured to transmit, based on the pharmaceutical benefits manager, the authorization with the reimbursement to the client device for the given plan entity and the quantity, the authorization and reimbursement independent of the quantity to prevent an assignment of an additional processor control number for different number of days supply associated with the quantity of the prescription drug.

The disclosed subject matter also provides an innovative pharmacy-based program that allows employees/plan members who take long term maintenance medications to have a choice between obtaining such medications from a mail order pharmacy or a local retail pharmacy outlet, by effectively balancing plan reimbursement and discount payments such that both types of pharmacies are compensated essentially equally, while taking into consideration the relative operational strengths and weaknesses of each type. The patient thus is pleased, by having a choice of pharmacies based on his/her own perceptions of the merits of each and particularly in not being deprived of such choice because of financial biases in the plan's provisions. The acquiring entity also is pleased, since the plan members are content and the plan costs are economically reasonable. The pharmacy industry as a whole also benefits, since undue biases toward mail order are avoided, pharmacies can effective participate in the overall dispensing of all medications and each part of the industry is able to compete on the basis of its merits of the customer service and value.

In its embodiments, the plan operates by having the PBM set a target cost for medications and dispensing services which it will pay according to contracts it enters into with the pharmacies, and similarly having contracts with its customers (the acquiring entities) as to the target costs and its management fees that it will charge the customers under the plan. A key component of the disclosed subject matter is that reimbursement rates are set that benefit the pharmacy, the acquiring entity and the consumer. The pharmacy target costs are based on a combination of industry-accepted medication cost schedules and negotiated discounts, calculated such that the payments to the pharmacies will all be substantially equal for a given patient's medication, dosage and quantity prescription, taking into account the different operating characteristics and costs of pharmacies versus mail order pharmacies in terms of factors such as patient contact and education, economies of scale in inventorying, staffing requirements and the like.

In many of its embodiments, the plan includes a method to ensure that the acquiring entity, the pharmacy and the patient are not disadvantaged. We have called this method the "true-up" feature. A lower of AWP or MAC price model is applied. At the conclusion of a set period of time, the reimbursement performance is measured and compared to a guaranteed value. If the value is above or below the targeted discount, the AWP or MAC prices are adjusted ("trued up") to compensate moving forward for the next set time period. These small adjustments are made every set time period to ensure performance balances to an overall guaranteed value. In this manner the acquiring entity benefits from the MAC pricing on individual generic products and benefits from assurances that the overall guaranteed performance is maintained, the pharmacy benefits by the assurance that it will be paid at an overall guaranteed discount performance number and the patient benefits by paying a co-payment that is reflective of the lower of MAC or AWP and thus is not disadvantaged by electing the one time 90-day fill as opposed to having the same prescription filled three separate times for a 30-day supply.

An additional aspect is the ability to simplify prescription requesting procedures for the pharmacies. When a pharmacy sends a prescription to a PBM for processing, they utilize a computer system and transmit on-line a request of payment to the PBM. This is called an on-line adjudicated claim. A pharmacy communicates to the PBM by sending an on-line adjudication claim to what is known in the industry as a "switch" company. There are two sets of numbers that are important to this transaction. The first is what is known as the "business identification number" (BIN). The BIN identifies the PBM that is processing the claim. The switch company recognizes this BIN and routes the claim to the appropriate PBM for processing. The second number is known as the PCN, described above. Once a claim has been routed to the appropriate PBM, the PCN directs the claim to the appropriate plan or acquiring entity within the PBM for processing. The adjudicated claim contains important information such as patient identification, drug and dosage, and days supply for which the medication is intended to be dispensed. The pharmacy enters this information and then transmits the claim electronically. Once routed to the PBM, the PBM reviews the claim and determines if the patient is eligible, if the drug is approved for dispensing, what portion the patient should pay as a co-payment, and at what rate the pharmacy should be reimbursed. In addition, the PBM verifies that the days supply is an approved benefit for the member. As noted in the Background, since the patient only presents one identification card, availability of different quantities and design benefits for the same medication with different PCNs can cause confusion at the pharmacy. The pharmacy staff member must decide whether to submit to the appropriate BIN the PCN for the 30-day benefit or the PCN for the 90-day benefit. If the incorrect PCN is used, the PBM will reject the claim until the PCN error can be corrected, thus delaying filling of the prescription for the consumer.

The disclosed subject matter eliminates the need for multiple PCNs for the same medication for a given acquiring entity. Under the present plan, each medication for a given acquiring entity has only a single PCN regardless of the quantity (number of days supply). The pharmacist need only provide the basic data of medication identification, dosage and quantity along with the single PCN for that medication and the BIN for that acquiring entity plan. Through editing procedures internal to the PBM itself, the PBM can review the claim and based on the days supply provided by the pharmacist, correctly apply the benefit structure for the member and the appropriate reimbursement to the pharmacy. This unique editing feature enables a pharmacy to have to select and submit only a single PCN for the patient's medication for review. This process saves time and confusion for the patient and the pharmacy and ensures a greater utilization of the 90-day benefit which saves the acquiring entity. This applies not only to pharmacies, which may have a only small staff to handle such administrative matters and thus appreciate the simplification of their tasks, but also large mail order pharmacies, since elimination of the need to select among multiple PCNs for many prescriptions may allow staff to be reduced or some staff members to be reassigned to other tasks.

The foregoing, together with other features and advantages of the disclosed subject matter, will become more apparent when referring to the following specification, claims and accompanying drawings.

BRIEF DESCRIPTION OF THE DRAWINGS

The disclosed subject matter will be better understood from the following detailed description of an exemplary embodiment of the disclosed subject matter, taken in conjunction with the accompanying drawings in which like reference numerals refer to like parts and in which.

DETAILED DESCRIPTION OF EXAMPLE EMBODIMENTS

When a patient receives a prescription for medication from a physician, the patient either goes to a retail pharmacy or utilizes mail order to have the prescription filled. If utilizing a retail pharmacy, the patient walks into the pharmacy and presents the prescription to a pharmacist or pharmacy staff member. The pharmacy enters the prescription into a computer, which sends the information to a telecommunications switch, or routing, company. Next, the switch company sends the information to the correct PBM with which the pharmacy has contracted for the type of prescription. The PBM determines the benefits the patient is eligible for, i.e., whether the prescription is eligible for fulfillment based on the terms of the acquiring entity plan that the patient is under. The PBM reports back through the switch company to confirm the amount of medication the patient is eligible for, copay amount if required, and certain safety messaging if appropriate. In most cases, a prescription is approved and filled without question or delay, since the consumer's prescription meets all of the applicable requirements of the plan that the patient is under. There are, however, a number of common reasons why a prescription may not be approved for fulfillment, which must be reported back to the pharmacy so that the patient can, if possible, make the necessary corrections or obtain further physician input to allow resubmission of the prescription.

The disclosed subject matter provides a system and method for a patient to go to either a retail pharmacy or a mail order pharmacy and have a prescription approved and filled, whether the prescription medication quantity is intended for 30 days or 90 days or any other prescribed time period. Additionally, the retail pharmacy only has to adjudicate the claim to a PBM under a single PCN to obtain a determination of eligibility and of the reimbursement rate. The pharmacist no longer has to determine which of multiple PCNs is correct for a particular plan (BIN) in order to get a prescription request adjudicated by the PBM. Further, since the plan of this disclosed subject matter essentially puts all pharmacies on equivalent footing, a patient can exercise his or her choice in selecting which pharmacy to patronize.

Figure 1:
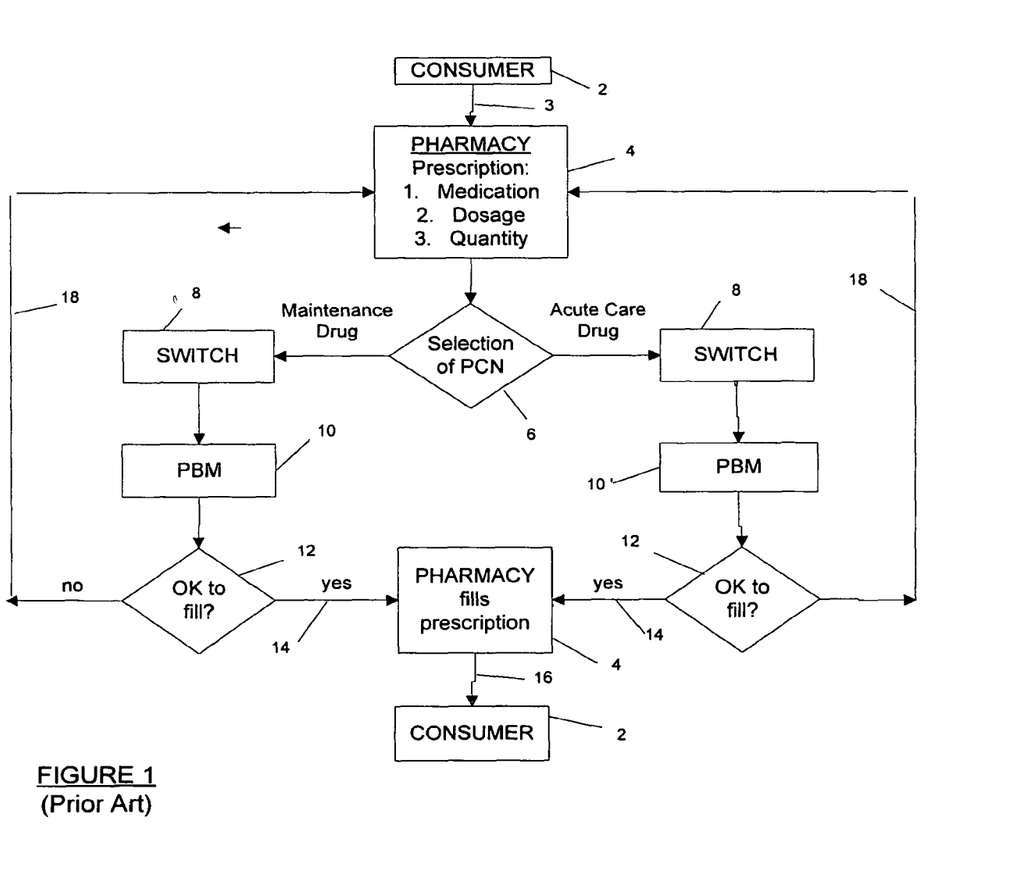
FIG. 1 is a process flow diagram showing the typical routing of a prescription approval and reimbursement request in many of the current prior art plan systems currently in the marketplace.

FIG. 1 outlines the course of a prescription request under many of the prior art commercial plans currently in the marketplace. A patient 2 at 3 brings a prescription from a physician to a pharmacy 4. The prescription identifies the medication to be dispensed, the dosage of each tablet or other dose unit, and the quantity of dose units to be dispensed. For the purposes of the discussion below, a short-term (acute care) dose unit quantity will be considered to be a 30-day quantity and a long-term (maintenance) dose unit quantity will be considered to be a 90-day quantity. The prescription may also indicate whether a brand name medication is required or a generic equivalent may be substituted. The pharmacist or pharmacy staff member selects what he/she believes to be the appropriate PCN for the consumer's plan based on the plan BIN at 6 and sends the request by computer to the switch (routing) company 8, which, based on the BIN and PCN provided by the pharmacist, routes the request to the designated PBM 10 or 10'. The recipient PBM 10 or 10' reviews the request at 12, and if all is in order in the request information and the prescription meets the plan's formulary and eligibility criteria, the PBM at 14 so notifies the pharmacy 4 and the pharmacy 4 fills at 16 fills the patient 2's prescription.

Such prior art systems may have numerous inherent or deliberate problem areas or biases. One as noted is the requirement that the pharmacy 4 must determine the correct PCN for the consumer's plan. An incorrect PCN designation will result in disapproval of the request and return to the pharmacy for correction at 18. Further, under many of the current plans, especially those in which the PBM owns a "captive" mail order pharmacy and a maintenance medication is involved, the patient 2 may be required or at least strongly urged financially to select as the pharmacy 4 only the PBMs captive mail order pharmacy, such that the consumer's potential choice of what pharmacy to patronize is curtailed or eliminated right at the entry 3 into the system. Such financial biasing may be done either by mandating use of a specific pharmacy 4 or by increasing a consumer's required copay or reducing the discount available to the patient if other than the captive pharmacy is used by the consumer. Such prior art systems are also often very difficult for PBMs to monitor for optimum performance because important decisions (such as selection of the PCN) are made at different points in the system by different people who may have greater or lesser understandings of the operation of the system.

Figure 2:
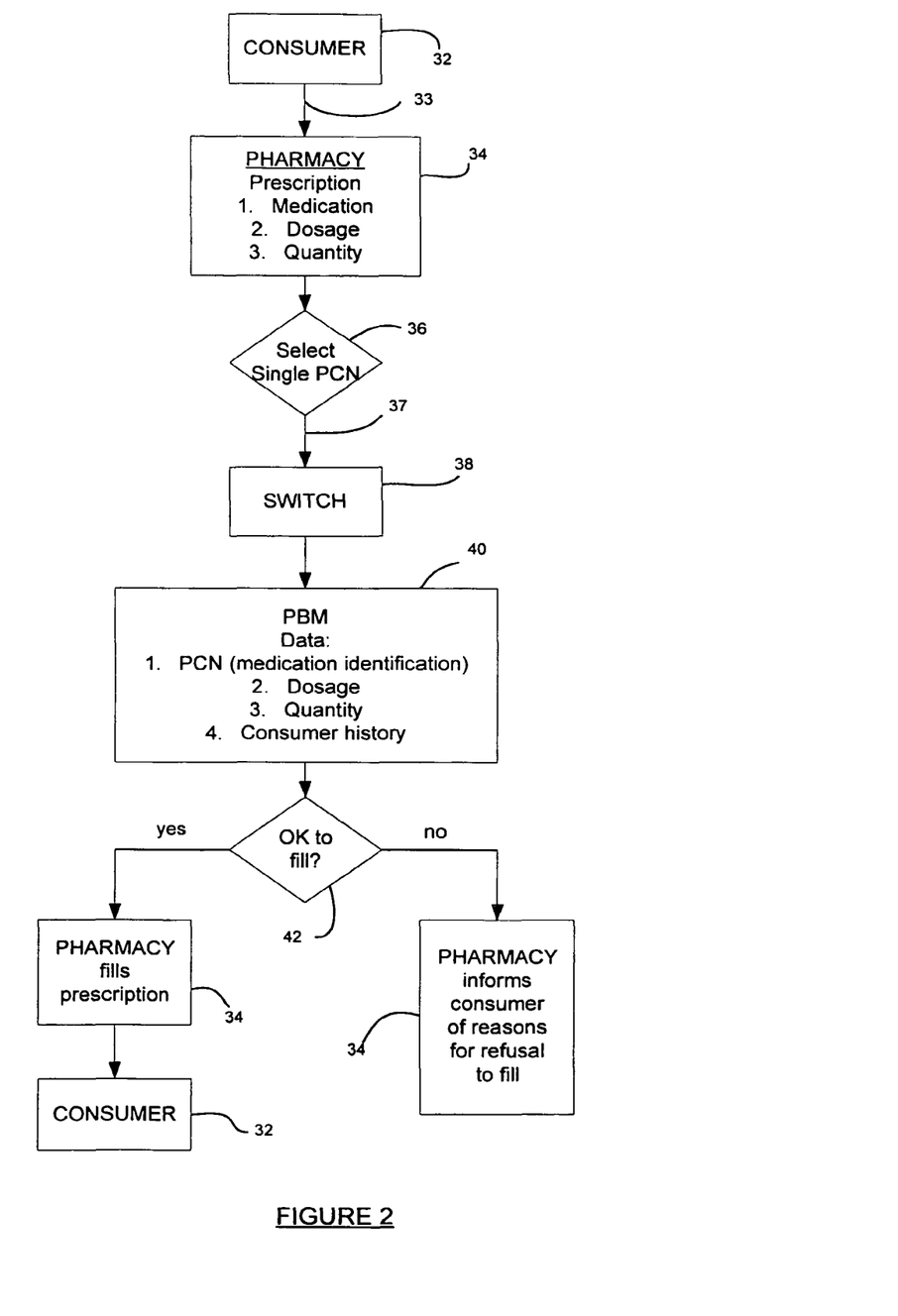
FIG. 2 is a process flow diagram showing the typical routing of a prescription approval and reimbursement request in the method of the disclosed subject matter.

The method of the disclosed subject matter is outlined in FIG. 2, and will immediately be seen to be much simpler, more direct for both the patient and pharmacy, and free of biases that would restrict a consumer's choice of pharmacy. It will also be seen that it is much easier to monitor for performance, since at each point the persons involved make decisions only as to those factors which are clearly within their areas of expertise. In the present system, patient (now designated 32) at 33 takes his/her prescription to any pharmacy 34 of his or her choice. Since under the present plan all pharmacies are will be compensated on a substantially equivalent basis for filling this consumer's particular prescription, there is no element of bias on the part of the pharmacy or the PBM of the consumer's plan for or against any type of pharmacy. At the pharmacy 34 the pharmacist or pharmacy staff member needs only to select a single PCN—the PCN assigned to the medication itself—at 36 and send that PCN, along with the dosage and quantity data, at 37 to the switch company 38 who in turn routes it to the single PBM 40 who handles all requests for that medication.

The PBM internally analyzes the request at 42. Knowing the medication itself from the single PCN, the PBM can then assess whether the dosage and quantity prescribed are within the limits of the plan's formulary, and whether filing of the prescription is timely based on the consumer's past prescription fulfillment history. The PBM may also assess whether dispensing of this prescribed medication is appropriate in view of other medications known by the PBM to have been prescribed previously to the consumer. Whether or not the PBM's internal analysis procedures involve assignment of further PCNs, subdivisions thereof, or other procedures in strictly for the PBM to decide, and does not affect the operation of this disclosed subject matter. Importantly, it does not affect the patient or the pharmacy and does not impose any burdens on them, in contrast to the case with the prior art systems. Once the PBM completes its assessment of the prescription request, it communicates approval or disapproval (with reasons) back to the pharmacy 34 either directly or through the switching company.

The present plan system functions by use by the PBM of contracted discounts and fulfillment service charges between the PBM and the various pharmacies who wish to participate in the plan. The function is best understood by reference to the Table below, in which an exemplary set of discounts, copays and fulfillment fees are presented. It will be understood that the values shown are exemplary only, and that discounts, copays and fees can and do vary widely depending on the contractual terms consented to by the parties to the various agreements. Commonly there may be different terms within a plan for different medication groups or even for different individual medications. Different pharmacies or pharmacy chains may also have different agreement terms with the same PBM, notwithstanding that all use the plan concept of the disclosed subject matter.

In the Table that follows, the disclosed subject matter is shown in the column at the far right with the current (prior art) retail pharmacy and mail order pharmacy plans being shown in the third and fourth columns from the left. Copays charges to patients are in the second column, and the Table differentiates between the reimbursement for brand name drugs and generic drugs, which reflects the standard industry practice. "AWP" means "average wholesale price" of a medication or medication group, whether brand name or generic, usually available from a single or limited number of producers, and is commonly a price determined on a national basis independently of the PBM, pharmacy or plan contracts. "MAC" means "maximum allowable cost" of a generic medication, which usually is calculated from consideration of marketplace prices for the medication from different producers. Such pricing data are commercially and publicly available from various sources. The data in the Table are generally presented as a total cost per dispensed dosage quantity, and are in the format of a "list price" such as AWP or MAC followed by the discount from that price that the PBM and the pharmacy have agreed to (e.g., "−15%") and by the fulfillment fee per transaction which the PBM will pay to the pharmacy. It is not uncommon for there to be no fulfillment fee ("+$0") especially in transactions involving generic drugs.

TABLE 1

Discount and Payment Comparisons

| Medication | Patient Copay | Retail Pharmacy 90 day quantity | Mail Order Pharmacy 90 day quantity | The Disclosed subject matter |
| --- | --- | --- | --- | --- |
| Brand Name Drugs | 20%, 30% | AWP − 15% + $2 (3 copays) | AWP − 20% + $0 (1-2.5 copays) | AWP − 20% + $0 (+1-2.5 copays) |
| Generic Drugs | 0%, 10% | Lower of: A) AWP − 15% + $2 B) MAC + $2 (3 copays) | AWP − 50% + $0 (1-2.5 copays) | Target is always AWP − 50% + $0 (with copays) which is obtained by using AWP − 25% + $0 and MAC + $0 in combination |
| Comments: | | Cannot usually compete on long-term prescription pricing and discounts | Usually does not accept short-term prescriptions | Puts retail and mail order pharmacies on equivalent basis for all drugs from patients' and acquiring entities' perspective |

It will be seen from the Table that a major effect of the claimed prescription plan as compared to the prior art is in the handling of reimbursements for generic drugs. Generic drug reimbursement represents a significant share of prescriptions dispenses, generally being about 50% of prescription dispensed nationally. It is also the portion of the industry which is most susceptible to control by the medical reimbursement plans, since there are numerous medication manufacturers for many of the generic drugs, which fosters competition between them, while most of the brand name (proprietary) drugs are available only from a single producer. Generic drugs save money for the acquiring entity, provide patients with the lowest copay option and typically provide the pharmacy with the highest profitability.

The disclosed subject matter focuses not on the quantity of medication to be dispensed (and thus on the acute care or maintenance purpose of the prescription) but rather on the cost/discount structure of the pharmacy reimbursement. Effectively the pharmacies are given the opportunity to compete for fulfillment of both long-term and short-term prescriptions, but equalizing the reimbursements available under the plan. The plan, unlike the prior art plans, does not bias patients toward the mail order pharmacies, which many PBMs have assumed must have larger economies of scale, staffing and other financial factors as compared to the pharmacies. Such assumptions may not always be correct, according to some studies, but the relative merits of the two types of pharmacies is not a factor in the disclosed subject matter, which instead is focused on giving the patient the ability to make his or her own evaluation and selection of which type of pharmacy to patronize. It will be seen from the Table that a PBM using the present plan will target a reimbursement rate generally comparable to the rate accorded to mail ordered pharmacies in the past, but does so in a manner which reflects and utilizes rate structures equally available to both types of pharmacies. This use of different criteria to achieve a similar rate level represents a completely novel and advantageous element of the disclosed subject matter. Thus rather than rigidly applying a single measurement based solely on AWP, as the prior art plans did, the present plan uses a blend of AWP and MAC criteria, and adjusts these as appropriate so that the overall reimbursement offered to pharmacies makes this plan competitive with the prior art plans with respect to the mail order pharmacies while, unlike prior art plans, also equally available and attractive to the pharmacies.

Patients can be adversely affected if a true-up process is not established, since without such a provision a patients copayments for a 90-day supply could exceed three times the traditional 30-day retail copayment.

Similar adjustments by the PBM can be negotiated and agreed to in contracts with pharmacies with respect to the dispensing fees to be paid under the plan. Prior art plans have worked on the basis that dispensing costs are higher for pharmacies because of staffing costs and lower volume over which to expense the per-patient dispensing costs. Increasing a retail pharmacy's proportion of dispensing of large quantity maintenance drug prescriptions offers an opportunity for the PBM and the retail pharmacy to reduce or eliminate the dispensing fee portion of reimbursement, thus reducing the costs to be passed along to the acquiring entity by the PBM.

An important optional (but preferred) element in the disclosed subject matter is a function of continually reviewing the performance of the pharmacies in cost control, and particularly in the area of cost reduction by increasing the proportion of lower cost generic drugs in the overall mix of dispensed drugs. In the past, mail order pharmacies and some mandate plans have accomplished this simply by requiring substitution of generics unless a physician has required otherwise. The disclosed subject matter also optionally allows for a particularly productive approach which involves education of the patients so that they recognize when generic medications are equally acceptable in their own personal health and treatment as are brand name drugs. Education is in the realm of both the PBM and the pharmacist, and the disclosed subject matter uses the involvement of both. Contracts with pharmacies can include provisions that encourage pharmacists to communicate with their patients about the value of generic drugs, which is especially effective in the retail pharmacy setting where the pharmacist and the patient meet directly. The PBM also can communicate the same message through its regular communications with acquiring entities and their employees and members. The pharmacy makes its highest profit margin dispensing the generic drug. The PBM that owns the mail order pharmacy may drive higher cost brands to maximize the formulary rebate income.

In keeping with this purpose, the present plan optionally but preferably includes not only the PBM's continual review of performance of all pharmacies participating in the plan, but also periodic adjustment of the discount and cost structures to reward those pharmacies who are operating at greater-than-expected performance and, conversely, to provide incentive to under-performing pharmacies to improve. This method, which we have designated "truing up" or the "true-up" feature, ensures that the acquiring entity, the pharmacy and the patient are not disadvantaged. A lower of AWP or MAC price model is applied. At the conclusion of a set period of time, the reimbursement performance is measured and compared to a guaranteed value. If the value is above or below the targeted discount for the period, the AWP or MAC price discounts are adjusted to compensate moving forward for the next set time period. If the drug mix has over performed, the reimbursement is increased, as for instance by reducing the discount taken by the PBM (e.g., from a 50% discount to a 49% discount), so that discounted amount paid to the pharmacy is increased and it therefore receives a greater income. On the other hand, if the drug mix has underperformed, the discount can be increased (e.g., from a 50% discount to a 51% discount) so that reimbursement—i.e., the discounted amount paid—is reduced, which it is expected will encourage the pharmacy to improve its performance over the next period so that its discount can be lowered and its reimbursement increased. Compiling performance data and making the appropriate analyses to allow such adjustments to be made require significant internal data collection and processing capabilities by the PBMs. However, such capabilities are already possessed by some PBMs and others can be expected to acquire similar capabilities in the near future, since having these small adjustments made every set time period (e.g., quarterly) ensure performance balances to an overall guaranteed value.

By use of the truing up feature, the acquiring entity benefits from the MAC pricing on individual generic products and benefits from assurances that the overall guaranteed performance is maintained, the pharmacy benefits by the assurance that it will be paid at an overall guaranteed discount performance number, and the patient benefits by paying a co-payment that is reflective of the lower of MAC or AWP and thus is not disadvantaged by electing the one-time 90 day fill as opposed to having the same prescription filled three times for 30-day supplies.

Separately, the plan of this disclosed subject matter also involves contractual agreements between the PBM and the acquiring entities who wish to provide the PBM's plan to their employees, members, or other affiliated people. Such acquiring entities are commonly business entities such as health plans, companies, partnerships or corporations, whether large, mid-sized or small, governments or governmental agencies, trade unions and non-governmental organizations or associations. Each acquiring entity contracts with the PBM for the specific pharmacy services and medication costs and fees that it is willing to reimburse, based on the PBM's having obtained discounted costs from the pharmacies, as well as the contracted fee that the acquiring entity is willing to pay the PBM for managing the plan for it and its employees or members. As with the pharmacy contracts, the acquiring entity contracts will also vary depending on what formulary a acquiring entity is willing to reimburse for, how many members or employees the acquiring entity has, and so forth.

It is to be expected that PBMs which have cost driven plans which focus primarily on mandating or influencing patients to use mail order pharmacies to fill maintenance prescriptions, especially those who own mail order pharmacies; will initially see little value in adopting the disclosed subject matter. However, it is anticipated that the present plan's focus on providing the ability to patients to be able to patronize the pharmacy of their choice for all of the prescription medication needs, whether acute care or maintenance medications, will be sufficiently attractive to such patients that they will encourage their employers or organizations as acquiring entities to obtain and adopt such plans. The employers and organizations, in turn, will demand of PBMs that they make such plans available to the acquiring entity community, in preference to mandated or biased plans. Under such conditions, it is to be expected that the plans of the disclosed subject matter will rapidly gain market share and enhance the ability of people to be able to influence or control their own costs of health care and prescription drugs.

Although several embodiments of the disclosed subject matter have has been described above by way of example only, it will be understood by those skilled in the field that numerous variations and modifications may be made to the disclosed embodiments without departing from the scope or spirit of the disclosed subject matter, as it is defined by the appended claims.

The invention claimed is:

1. An electronic system for routing claims, the system comprising:
a computer network;
a client device communicatively coupled to the computer network, the client device configured to receive order information representative of a prescription drug prescribed for a patient, the order information including a given plan entity and a quantity of the prescription drug;
a telecommunications switch communicatively coupled to the client device via the computer network, the telecommunications switch configured to receive one or more processor control numbers (PCNs) associated with the order information and route the order information based on the one or more PCNs, a PCN being independent of the quantity of the prescription drug and the PCN uniquely identifying the prescription drug, the telecommunications switch being configured to route the one or more PCNs to at least one of a first pharmaceutical benefits manager (PBM) system and a second PBM system, the first PBM system and the second PBM system being configured to approve the prescription drug based on whether the patient is eligible; and
a controller with a pharmaceutical benefits manager communicatively coupled to the client device and the telecommunications switch via the computer network, the pharmaceutical benefits manager configured to approve the prescription drug and configured to determine a reimbursement, the controller configured to:
receive, from the telecommunications switch, the order information based on a single PCN and a business identification number, the business identification number configured to identify the pharmaceutical benefits manager among the first PBM system and the second PBM system;
determining, using the pharmaceutical benefits manager, the reimbursement based on the order information and whether the patient is eligible;
determining, using the pharmaceutical benefits manager, an authorization for the prescription drug with the reimbursement based on the single PCN; and
transmitting the authorization with the reimbursement to the client device for the given plan entity and the quantity, the authorization and reimbursement independent of the quantity to prevent an assignment of an additional PCN for different number of days supply associated with the quantity of the prescription drug.

2. A non-transitory computer-readable storage medium storing instructions that, when executed by a processor, cause the processor to perform operations comprising:
receiving, using an pharmaceutical benefits manager and from a telecommunications switch communicatively coupled to a client device via a computer network, order information based on a single processor control number (PCN) and a business identification number, the telecommunications switch configured to receive one or more PCNs associated with the order information and route the order information based on the one or more PCNs, the order information representative of a prescription drug prescribed for a consumer and including a given plan entity and a quantity of the prescription drug, the processor control number being independent of the quantity of the prescription drug and a PCN uniquely identifying the prescription drug, the PCN having been forwarded from the client device to the telecommunications switch, the telecommunications switch being configured to route the one or more PCNs to at least one of a first pharmaceutical benefits manager (PBM) system and a second PBM system, the first PBM system and the second PBM system being configured to approve the prescription drug based on whether a patient is eligible, and the business identification number configured to identify an electronic benefits manager among the first PBM system and the second PBM system;
determining, using the pharmaceutical benefits manager, a reimbursement based on the order information and whether the patient is eligible;
determining, using the pharmaceutical benefits manager, an authorization for the prescription drug with the reimbursement based on the single PCN; and
transmitting the authorization with the reimbursement to the client device for the given plan entity and the quantity, the authorization and reimbursement independent of the quantity to prevent an assignment of an additional PCN for different number of days supply associated with the quantity of the prescription drug.

3. A system including a pharmaceutical benefits manager, the system comprising:
at least one data processor; and
at least one memory storing instructions, which when executed by at least one data processor, result in operations comprising:
receive, using the pharmaceutical benefits manager and from a telecommunications switch communicatively coupled to a client device via a computer network, order information based on a single processor control number (PCN) and a business identification number, the telecommunications switch configured to receive one or more PCNs associated with the order information and route the order information based on the one or more PCNs, the order information representative of a prescription drug prescribed for a consumer and including a given plan entity and a quantity of the prescription drug, the processor control number being independent of the quantity of the prescription drug and a PCN uniquely identifying the prescription drug, the telecommunications switch being configured to route the one or more PCNs to at least one of a first pharmaceutical benefits manager (PBM) system and a second PBM system, the first PBM system and the second PBM system being configured to approve the prescription drug based on whether a patient is eligible, and the business identification number configured to identify an electronic benefits manager among the first PBM system and the second PBM system;

determining, using the pharmaceutical benefits manager, a reimbursement based on the order information and whether the patient is eligible;

determining, using the pharmaceutical benefits manager, an authorization for the prescription drug with the reimbursement based on the single PCN; and transmitting the authorization with the reimbursement to the client device for the given plan entity and the quantity, the authorization and reimbursement independent of the quantity to prevent an assignment of an additional PCN for different number of days supply associated with the quantity of the prescription drug.

4. The system of claim 1, wherein the reimbursement is equal to the lesser of a first value calculated based on a maximum allowable cost (MAC) and a second value calculated based on an average wholesale price (AWP).

5. The non-transitory computer-readable storage medium of claim 2, wherein the reimbursement is equal to the lesser of a first value calculated based on a maximum allowable cost (MAC) and a second value calculated based on an average wholesale price (AWP).

6. The system of claim 3, the reimbursement is equal to the lesser of a first value calculated based on a maximum allowable cost (MAC) and a second value calculated based on an average wholesale price (AWP).

7. The system of claim 4, wherein at least one of the MAC and the AWP is adjusted in response to a difference between a guaranteed value and a reimbursement performance for a plurality of orders over a time period.

8. The non-transitory computer-readable storage medium of claim 5, wherein at least one of the MAC and the AWP is adjusted in response to a difference between a guaranteed value and a reimbursement performance for a plurality of orders over a time period.

9. The system of claim 6, wherein at least one of the MAC and the AWP is adjusted in response to a difference between a guaranteed value and a reimbursement performance for a plurality of orders over a time period.

10. A computer-implemented method comprising:

receiving, using an pharmaceutical benefits manager and from a telecommunications switch communicatively coupled to a client device via a computer network, order information based on a single processor control number (PCN) and a business identification number, the telecommunications switch configured to receive one or more PCNs associated with the order information and route the order information based on the one or more PCNs, the order information representative of a prescription drug prescribed for a consumer and including a given plan entity and a quantity of the prescription drug, the processor control number being independent of the quantity of the prescription drug and a PCN uniquely identifying the prescription drug, the PCN having been forwarded from the client device to the telecommunications switch, the telecommunications switch being configured to route the one or more PCNs to at least one of a first pharmaceutical benefits manager (PBM) system and a second PBM system, the first PBM system and the second PBM system being configured to approve the prescription drug based on whether a patient is eligible, and the business identification number configured to identify an electronic benefits manager among the first PBM system and the second PBM system;

determining, using the pharmaceutical benefits manager, a reimbursement based on the order information and whether the patient is eligible;

determining, using the pharmaceutical benefits manager, an authorization for the prescription drug with the reimbursement based on the single PCN; and transmitting the authorization with the reimbursement to the client device for the given plan entity and the quantity, the authorization and reimbursement independent of the quantity to prevent an assignment of an additional PCN for different number of days supply associated with the quantity of the prescription drug.

11. The method of claim 10, wherein the reimbursement is equal to the lesser of a first value calculated based on a maximum allowable cost (MAC) and a second value calculated based on an average wholesale price (AWP).

12. The method of claim 11, wherein at least one of the MAC and the AWP is adjusted in response to a difference between a guaranteed value and a reimbursement performance for a plurality of orders over a time period.

* * * * *